United States Patent
Kato et al.

[11] Patent Number: 5,817,689
[45] Date of Patent: Oct. 6, 1998

[54] INDOLE DERIVATIVES HAVING A 2-PHENYL-ETHANOLAMINO-SUBSTITUTED LOWER ALKYL GROUP AT THE 2-OR 3-POSITION THEREOF

[75] Inventors: Shiro Kato, Sakai; Hiroshi Harada, Suita; Yoshimi Hirokawa, Ikoma; Naoyuki Yoshida, Sakai; Hitoshi Kawashima, Osaka, all of Japan

[73] Assignee: Dainippon Pharmaceutical Co., Ltd., Osaka, Japan

[21] Appl. No.: 836,983

[22] PCT Filed: Nov. 27, 1995

[86] PCT No.: PCT/JP95/02400

§ 371 Date: May 29, 1997

§ 102(e) Date: May 29, 1997

[87] PCT Pub. No.: WO96/16938

PCT Pub. Date: Jun. 6, 1996

[30] Foreign Application Priority Data

Nov. 29, 1994 [JP] Japan ..................... 6-321402

[51] Int. Cl.⁶ .......................... A61K 31/40; C07D 209/14
[52] U.S. Cl. .......................... 514/415; 514/411; 514/866; 514/909; 548/431; 548/506
[58] Field of Search .................. 548/506, 431; 514/411, 415

[56] References Cited

U.S. PATENT DOCUMENTS 4,055,658 10/1977 Kreighbaum et al. .................. 424/304

FOREIGN PATENT DOCUMENTS

| 6-345731 | 12/1994 | Japan . |
| 861428 | 7/1959 | United Kingdom . |
| 2135883 | 9/1984 | United Kingdom . |

OTHER PUBLICATIONS

Bobzin et al., "Aromatic Alkaloids from the Marine Sponge Chelonaplysilla", J. Org. Chem., 56, 4403–4407 (1991).
Chemical Abstract, 78, 431, 71665s (1973).
Clifton et al., "Arylethanolamines Derived from Salicylamide with α–and β–Adrenoceptor Blocking Activities. Preparation of Lebetalol, Its Enantiomers, and Related Salicylamides", 25, 670–679 (1982).
Jackman et al., "Some tryptamine derivatives: 1–aryloxy–3–[(2–indol–3'–ylethyl)amino]propan–2–ols", J. Pharm. Pharmacol., 17, 742–746 (1965).
Chemical Abstract, 96, 726, 142543k (1982).
Chemical Abstract, 109, 666, 128763n (1988).
Kato et al., CA 122:239540, May 8, 1995.
Patent Abstracts of Japan for JP 06345731, 1994.

*Primary Examiner*—Joseph McKane
*Assistant Examiner*—Laura L. Stockton
*Attorney, Agent, or Firm*—Foley & Lardner

[57] ABSTRACT

An indole derivative of the formula:

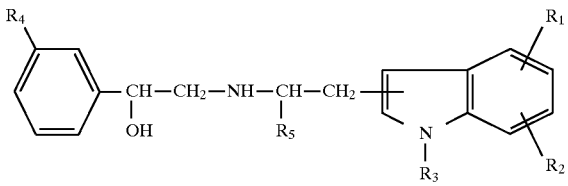

wherein $R_1$ is lower alkoxy, lower alkoxycarbonyl-lower alkoxy, carboxy-lower alkoxy, lower alkoxycarbonyl, phenyl-lower alkoxy, lower alkyl being optionally substituted by hydroxy, di-lower alkylaminosulfonyl, etc., $R_2$ is hydrogen, halogen, lower alkoxy, lower alkoxycarbonyl-lower alkoxy, carboxy-lower alkoxy, etc., $R_3$ is hydrogen or lower alkyl, $R_4$ is halogen or trifluoromethyl, $R_5$ is lower alkyl, or a salt thereof, these compounds being potent $\beta_3$-adrenergic receptor-stimulating agent with excellent adrenoceptor selectivity, and being useful in the prophylaxis or treatment of obesity or diabetes mellitus.

25 Claims, No Drawings

INDOLE DERIVATIVES HAVING A 2-PHENYL-ETHANOLAMINO-SUBSTITUTED LOWER ALKYL GROUP AT THE 2-OR 3-POSITION THEREOF

This application is a 371 of PCT/JP95/02400 filed Nov. 27, 1995.

TECHNICAL FIELD

The present invention relates to a novel indole derivative having a potent $\beta_3$-adrenergic receptor-stimulating activity with excellent adrenoceptor selectivity.

BACKGROUND ART

It has been known that β-receptor of sympathetic nerve has two sub-types, i.e. $\beta_1$-receptor and $\beta_2$-receptor. At the present, $\beta_1$-adrenergic receptor-stimulating agents have been clinically used as a cardiac function promoter or a vasopressor, and $\beta_2$-adrenergic receptor-stimulating agents have been used as a bronchodilator, respectively.

Recently, there has been found and isolated $\beta_3$-adrenergic receptor as the third subtype of β-adrenergic receptor, which is different from the above two subtypes [Emorine, L. J. et al; Science, 245, 1118–1121 (1989)]. The $\beta_3$-adrenergic receptor exists at brown adipose cells, and has been estimated to show a thermogenetic activity by decomposing lipids of white adipose cells adhering to the subcutaneous tissues or the internal organs, and hence, $\beta_3$-adrenergic receptor has been suggested to be connected with one of the causes of obesity. Besides, it has been reported that the crisis of the non-insulin-dependent diabetes mellitus may also be related with $\beta_3$-adrenergic receptor.

When a $\beta_3$-adrenergic receptor-stimulating agent acts on the $\beta_1$-adrenergic receptor and $\beta_2$-adrenergic receptor subtypes as well, there might be some side effects such as hyperfunction of heart, tremor of hands and foot, etc. Thus, it has been desired to develop a drug having a potent $\beta_3$-adrenergic receptor-stimulating activity but having no $\beta_1$-adrenergic receptor- and $\beta_2$-adrenergic receptor-stimulating activities, or having a weak $\beta_1$- and $\beta_2$-adrenergic receptor-stimulating activity. In the present description and claims, a compound having such properties is occasionally expressed as "a compound having an excellent adrenoceptor selectivity".

As a $\beta_3$-adrenergic receptor-stimulating agent, there have been disclosed BRL35135 {(R*,R*)-(±)-[4-[2-[2-(3-chlorophenyl)-2-hydroxyethylamino]-propyl]phenoxy] acetic acid methyl ester hydrobromide; Japanese Patent Second Publication (Kokoku) No. 26744/1988 and European Patent Publication No. 23385}, SR-58611A {(R,S)-N-(7-ethoxycarbonylmethoxy-1,2,3,4-tetrahydronaphth-2-yl)-2-(3-chlorophenyl)-2-hydroxyethanamine hydrochloride; Japanese Patent First Publication (Kokai) No. 66152/1989 and European Patent Publication No. 255415}, etc. However, these BRL35135 and SR-58611A are completely different from the compounds of the present invention as mentioned below in that these compounds are not indole derivatives.

The indole compounds as listed in Table 1 are also known.

TABLE 1

| Chemical Structure | Pharmacological Activity | Literature |
|---|---|---|
| HO—[phenyl(NHSO₂CH₃)]—CH(OH)—CH₂—NH—CH(CH₃)—CH₂—[indol-yl] | $\beta_2$-Adrenergic receptor-stimulating activity | German Patent Publication No. 3407861 |
| HO—[phenyl(HO)]—CH(OH)—CH₂—NH—CH(CH₃)—CH₂—[indol-yl] | Central nervous system inhibitory activity | British Patent Publication No. 861,428 |
| CH₃O—[phenyl(Br)]—CH(OH)—CH₂—NH—CH₂—CH₂—[indol-yl] | Antibacterial activity | J. Org. Chem. 56 4403–4407 (1991) |
| HO—[phenyl(CH₂OH)]—CH(OH)—CH₂—NH—CH(CH₃)—CH₂—[indol-yl] | $\beta_2$-Adrenergic receptor-stimulating activity | Japanese Patent Second Publication (Kokoku) No. 2653/1971 |

TABLE 1-continued

| Chemical Structure | Pharmacological Activity | Literature |
| --- | --- | --- |
| 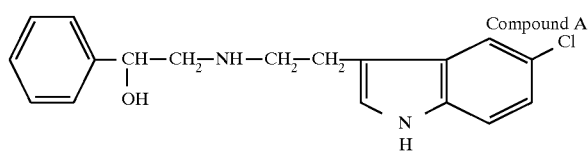 | $\beta_2$-Adrenergic receptor-stimulating activity | Japanese Patent First Publication (Kokai) No. 139041/1977 |
| 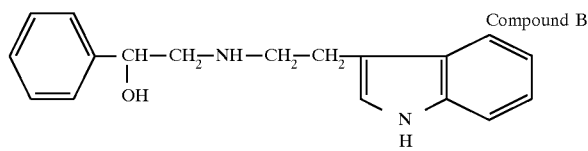 | $\beta_2$-Adrenergic receptor-stimulating activity | J. Med. Chem. 25, 670–379 (1982) |

However, these compounds are chemical-structurally different from the compounds of the present invention in having two substituents on the benzene ring and having no-substituent on the indole nucleus. Besides, these literatures have never suggest that these compounds have $\beta_3$-adrenergic receptor-stimulating activity.

The following compounds are known to have a more similar chemical structure to the compounds of the present invention than the compounds as listed in Table 1.

For example, J. Pharm. Phamacol., 17, 742–746 (1965) discloses the following Compound A.

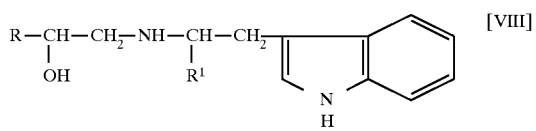
Compound A

Acta. Polon. Pharm., 38, 407–410 (1981) (Chem. Abstr., 96, 142543k (1982)) discloses the following Compound B.

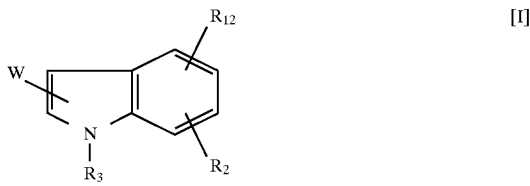
Compound B

The above Compounds A and B have different chemical structures from the present compounds in having no substituent on the benzene ring and having no substituent corresponding to the substituent $R_5$ of the present compounds as mentioned below. Besides, these literatures never teach or even suggest any pharmacological activities of Compounds A and B.

Further, Chem. Abstr., 109, 128763n (1988) discloses an N-indolylalkyl-amino-1-aryl-substituted alkanol derivative of the following formula [VIII]:

[VIII]

wherein R is a phenyl group, m- or p-nitrophenyl group, etc., and $R^1$ is a hydrogen atom or a methyl group.

The above compound has a different chemical structure from the present compounds in that the substituent on the benzene ring is a nitro group, and in that it has no substituent on the indole nucleus. The compound of the above formula [VIII] especially includes the following Compound C.

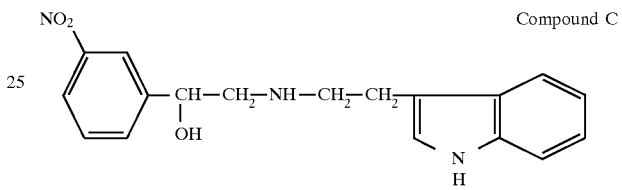
Compound C

The compound of the present invention is more superior as a $\beta_3$-adrenergic receptor-stimulating agent to the above Compounds A, B and C as shown in the pharmacological experiments as mentioned below.

Thus, an object of the present invention is to provide a novel indole derivative having a potent $\beta_3$-adrenergic receptor-stimulating activity with excellent adrenoceptor selectivity, or a salt thereof.

DISCLOSURE OF INVENTION

The present invention relates to an indole derivative of the following formula [I]:

[I]

wherein $R_1$ is a lower alkyl group being optionally substituted by a hydroxy group, a phenylsulfonylamino group, a lower alkylsulfonylamino group, a mono- or di-lower alkylaminosulfonyl group, or a group selected from the following (a) to (d), or combines with $R_2$ to form a methylenedioxy group, said methylenedioxy group being optionally substituted by a carboxyl group or a lower alkoxycarbonyl group, (a) a group of the formula: —X—Ra (wherein X is O, S or NH, Ra is a hydrogen atom or a lower alkyl group, provided that when X is S, then Ra is a lower alkyl group);

(b) a group of the formula:

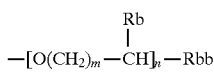

(wherein Rb is a hydrogen atom, a lower alkyl group, a lower alkoxycarbonyl group or a carboxyl group, Rbb is a lower alkoxycarbonyl group or a carboxyl group, m is an integer of 0 to 3, and n is 0 or 1);

(c) a group of the formula:—$O(CH_2)_p$—Rc (wherein Rc is a lower alkanoyl group, a hydroxy group, a cyano group, a phenyl group, a mono- or di-lower alkylaminocarbonyl group, or a group of the formula:

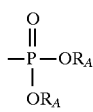

(wherein $R_A$ is a hydrogen atom or a lower alkyl group), and p is an integer of 1 to 4);

(d) a group of the formula:—Y—$(CH_2)_q$—Rd (wherein Y is NH or S, Rd is a carboxyl group or a lower alkoxycarbonyl group, q is an integer of 1 to 4);

$R_2$ is a hydrogen atom, a halogen atom, a lower alkyl group being optionally substituted by a hydroxy group, a hydroxy group, a lower alkoxy group, or a group of the above (b) or (c), or combines with $R_1$ to form a methylenedioxy group, said methylenedioxy group being optionally substituted by a carboxyl group or a lower alkoxycarbonyl group;

$R_3$ is a hydrogen atom or a lower alkyl group;

W is a group of the formula [II] which bonds to the 2- or 3-position of the indole nucleus:

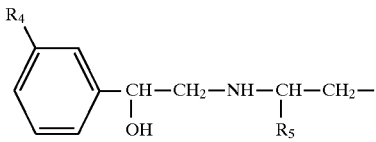

wherein $R_4$ is a halogen atom or a trifluoromethyl group, $R_5$ is a lower alkyl group, or a salt thereof.

The structural characteristic features of the compounds [I] of the present invention are:

(1) having a specific atom or a specific group on the 3-position of the benzene ring in the substituent W;

(2) the substituent $R_5$ being a lower alkyl group;

(3) having specific substituents $R_1$ and $R_2$ on the 4- to 7-positions of the indole nucleus;

(4) having the substituent W on the 2- or 3-position of the indole nucleus.

The potent $\beta_3$-adrenergic receptor-stimulating activity and the excellent adrenoceptor selectivity of the compounds of the present invention are based on the above structural characteristic features of the present compounds or a combination thereof.

The terms used in the present description and claims are explained below.

The group appended with "lower" means ones having 1 to 4 carbon atoms. The "lower alkyl group" includes, for example, methyl, ethyl, propyl, isopropyl, butyl, isobutyl, sec-butyl, tert-butyl, etc., but methyl, ethyl, propyl and isopropyl are more preferable. The "lower alkyl group substituted by a hydroxy group" includes, for example, hydroxymethyl, 2-hydroxyethyl, etc. The "lower alkylsulfonylamino group" includes, for example, methylsulfonylamino, ethylsulfonylamino, etc. The "mono- or di-lower alkylaminosulfonyl group" includes, for example, monomethylaminosulfonyl, dimethylaminosulfonyl, monoethylaminosulfonyl, diethylaminosulfonyl, etc. The "lower alkoxycarbonyl group" includes, for example, methoxycarbonyl, ethoxycarbonyl, propoxycarbonyl, butoxycarbonyl, etc. The "lower alkanoyl group" includes, for example, acetyl, propionyl, etc. The "mono- or di-lower alkylaminocarbonyl group" includes, for example, methylaminocarbonyl, dimethylaminocarbonyl, methylethylaminocarbonyl, etc. The "halogen atom" is fluorine, chlorine, bromine, iodine, and preferable one is fluorine, chlorine, bromine, and more preferable one is fluorine and chlorine. The "lower alkoxy group" includes, for example, methoxy, ethoxy, propoxy, isopropoxy, butoxy, isobutoxy, sec-butoxy, tert-butoxy, etc. The "lower alkoxycarbonyl-lower alkoxy group" includes, for example, methoxycarbonylmethoxy, 1-methoxycarbonylethoxy, 2-methoxycarbonylethoxy, 1-methoxycarbonylpropoxy, 3-methoxycarbonylpropoxy, etc. The "carboxy-lower alkoxy group" includes, for example, carboxymethoxy, 1-carboxyethoxy, 2-carboxyethoxy, 1-carboxypropoxy, 3-carboxypropoxy, etc. The "phenyl-lower alkoxy group" includes, for example, benzyloxy, phenethyloxy, etc.

The salt of the present compounds of the formula [I] is, for example, an acid addition salt thereof, and especially a pharmaceutically acceptable acid addition salt is preferable. The acid addition salt includes, for example, salts with an inorganic acid such as hydrochloric acid, hydrobromic acid, hydroiodic acid, sulfuric acid, phosphoric acid, and salts with an organic acid such as oxalic acid, maleic acid, fumaric acid, lactic acid, malic acid, citric acid, tartaric acid, benzoic acid, methanesulfonic acid, etc. Besides, the compounds of the present invention having a carboxyl group in the definition for the substituent $R_1$ or $R_2$ may exist in the form of an alkali metal salt or a salt with an organic base, for example, a salt with an alkali metal such as sodium, potassium, etc., or a salt with an organic base such as triethylamine, tributylamine, diisopropylethylamine, N-methylmorpholine, dicyclohexylamine, etc.

These acid addition salts, alkali metal salts or salts with an organic base may exist in the form of a hydrate or a solvate thereof, and the present invention also includes these hydrates and solvate as well.

The compound of the present invention of the formula [I] has two asymmetric carbon atoms. That is, in the formula [II], the carbon atom to which the hydroxy group bonds, and the carbon atom to which $R_5$ bonds are asymmetric carbon atoms. Thus, the compound of the present invention has four stereoisomers, and the present invention also includes these optically active compounds, racemic compounds, and a mixture thereof.

The preferable compound of the present invention is a compound of the formula [I] wherein the substituent W bonds to the 3-position of the indole nucleus, i.e. a compound of the formula [I-a]:

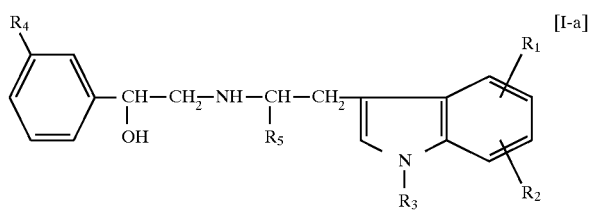

[I-a]

wherein $R_1$, $R_2$, $R_3$, $R_4$ and $R_5$ are the same as defined above, or a salt thereof. Among them, the more preferable compound of the present invention is the compound of the formula [I-a] wherein $R_1$ bonds to the 5-, 6- or 7-position of the indole nucleus, and $R_2$ is a hydrogen atom, or a salt thereof, or the compound of the formula [I-a] wherein $R_2$ is groups other than a hydrogen atom, and one of $R_1$ and $R_2$ bonds to the 6-position of the indole nucleus, and the other bonds to the 7-position thereof, or a salt thereof.

The other preferable compound of the present invention is an indole derivative of the formula [I-a] wherein $R_1$ is a lower alkyl group substituted by a hydroxy group, a phenylsulfonylamino group, a lower alkylsulfonylamino group, a di-lower alkylaminosulfonyl group, or a group of the following (a), (b-1), (c-1) or (d);

(a) a group of the formula:—X—Ra (wherein X and Ra are the same as defined above);

(b-1) a group of the formula:

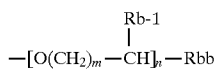

(wherein Rb-1 is a hydrogen atom or a lower alkyl group, Rbb, m and n are the same as defined above);

(c-1) a group of the formula:—O(CH$_2$)$_p$—Rc-1(wherein Rc-1 is a lower alkanoyl group, a phenyl group, a mono-lower alkylaminocarbonyl group, and p is the same as defined above);

(d) a group of the formula:—Y—(CH$_2$)$_q$—Rd (wherein Y, Rd and q are the same as defined above);

$R_2$ is a hydrogen atom, a halogen atom, a lower alkyl group being optionally substituted by a hydroxy group, a hydroxy group, a lower alkoxy group, or a group of the above (b-1) or (c-1), or a salt thereof. Among the above compounds, the further preferable compound is an indole derivative of the formula [I-a] wherein $R_1$ is a lower alkoxy group, a lower alkyl group, a lower alkoxycarbonyl group, a lower alkoxycarbonyl-lower alkoxy group, a carboxy-lower alkoxy group, a phenyl-lower alkoxy group or a di-lower alkylaminosulfonyl group, $R_2$ is a hydrogen atom, a halogen atom, a lower alkoxy group, a lower alkyl group, a lower alkoxycarbonyl group, a lower alkoxycarbonyl-lower alkoxy group, a carboxy-lower alkoxy group or a phenyl-lower alkoxy group, $R_3$ is a hydrogen atom, $R_4$ is a halogen atom, and $R_5$ is a methyl group, or a salt thereof.

The especially preferable compound is an indole derivative of the formula [I-a] wherein $R_1$ is methoxy group, ethoxy group, propoxy group, isopropoxy group, methyl group, methoxycarbonyl group, methoxycarbonylmethoxy group, carboxymethoxy group, benzyloxy group, or dimethylaminosulfonyl group, $R_2$ is a hydrogen atom or methoxy group, $R_3$ is a hydrogen atom, $R_4$ is a chlorine atom, $R_5$ is methyl group, or a salt thereof.

The most preferable compound of the present invention is an indole derivative of the formula [I-a] wherein $R_1$ is methoxy group, ethoxy group, methoxycarbonyl group, methoxycarbonylmethoxy group or a carboxylmethoxy group which bonds to the 6- or 7-position of the indole nucleus, $R_2$ and $R_3$ are a hydrogen atom, $R_4$ is a chlorine atom, $R_5$ is methyl group, or a salt thereof.

The representatives of the most preferable compounds are;

(1) 2-[3-(7-Methoxyindol-3-yl)-2-propylamino]-1-(3-chlorophenyl)ethanol (2) 2-[3-(7-Ethoxyindol-3-yl)-2-propylamino]-1-(3-chlorophenyl)ethanol (3) 2-[3-(7-Methoxycarbonylmethoxyindol-3-yl)-2-propylamino]-1-(3-chlorophenyl)ethanol (4) 2-[3-(7-Carboxymethoxyindol-3-yl)-2-propylamino]-1-(3-chlorophenyl)ethanol and optical isomers thereof, or salts thereof.

The representatives included in the present invention are the compounds as listed in Tables 2, 3 and 4, and salts thereof.

TABLE 2

| $R_1$ | $R_4$ | $R_1$ | $R_4$ |
|---|---|---|---|
| 6-OH | Cl | 7-OC$_2$H$_4$COOH | Cl |
| 6-COOH | Cl | 7-OCH(CH$_3$)$_2$ | Cl |
| 6-OCH$_2$COCH$_3$ | Cl | 7-OC$_2$H$_4$COOCH$_3$ | Cl |
| 6-OCH$_2$CONHCH$_3$ | Cl | 7-OCH$_2$COCH$_3$ | Cl |
| 6-SCH$_2$COOH | Cl | 7-OCH$_2$CONHCH$_3$ | Cl |
| 6-SCH$_2$COOCH$_3$ | Cl | 7-OCH$_2$CH$_2$OH | Cl |
| 6-NHCH$_2$COOH | Cl | 7-OCH$_2$CN | Cl |
| 6-NHCH$_2$COOCH$_3$ | Cl | 7-OCH(COOH)$_2$ | Cl |
| 6-NHSO$_2$CH$_3$ | Cl | 7-OCH(COOCH$_3$)$_2$ | Cl |
| 6-NHSO$_2$Ph | Cl | 7-SCH$_3$ | Cl |
| 7-OH | Cl | 7-SCH$_2$COOH | Cl |
| 7-SCH$_2$COOCH$_3$ | Cl | 7-CH$_2$OH | Cl |
| 7-NHCH$_2$COOCH$_3$ | Cl | 7-COOH | Cl |
| 7-NHCH$_2$COOH | Cl | 7-COOCH$_3$ | Cl |
| 7-NHSO$_2$Ph | Cl | 7-OCH(CH$_3$)COOH | Cl |
| 7-NHSO$_2$CH$_3$ | Cl | 7-OCH(CH$_3$)COOCH$_3$ | Cl |
| 7-NH$_2$ | Cl | 7-SO$_2$N(CH$_3$)$_2$ | Cl |
| 7-OCH$_3$ | CF$_3$ | 6-COOCH$_3$ | CF$_3$ |
| 7-OC$_2$H$_5$ | CF$_3$ | 6-OCH$_2$COOH | CF$_3$ |
| 7-COOCH$_3$ | CF$_3$ | 6-OCH$_2$COOCH$_3$ | CF$_3$ |
| 7-OCH$_2$COOH | CF$_3$ | 7-OCH$_2$COOCH$_3$ | CF$_3$ |
| 7-OCH$_3$ | Cl | 7-OC$_2$H$_5$ | Cl |
| 6-OCH$_3$ | Cl | 7-OCH$_2$Ph | Cl |
| 6-CH$_3$ | Cl | 7-CH$_3$ | Cl |
| 6-OCH$_2$COOCH$_3$ | Cl | 6-COOCH$_3$ | Cl |
| 4-OCH$_3$ | Cl | 4-CH$_3$ | Cl |
| 6-SO$_2$N(CH$_3$)$_2$ | Cl | 6-OCH$_2$COOH | Cl |
| 7-OCH$_2$COOCH$_3$ | Cl | 6-CH$_2$OH | Cl |
| 7-O(CH$_2$)$_2$CH$_3$ | Cl | 7-OCH$_2$COOH | Cl |

TABLE 3

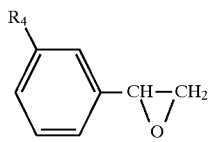

| R1 | R2 | R1 | R2 |
|---|---|---|---|
| $OCH_3$ | F | $OCH_3$ | $OC_2H_4COOCH_3$ |
| $OCH_3$ | $OCH_2COOH$ | $C_2H_5$ | F |
| $OCH_3$ | $C_2H_5$ | $C_2H_5$ | $OCH_3$ |
| $OCH_3$ | OH | $C_2H_5$ | $OC_2H_4COOH$ |
| $OCH_3$ | $OCH(CH_3)COOH$ | $C_2H_5$ | $OC_2H_5$ |
| $OCH_3$ | $OCH_2COOCH_3$ | $C_2H_5$ | $OCH_2COOH$ |
| $OCH_3$ | $OCH(CH_3)COOCH_3$ | $OCH_2COOH$ | $OC_2H_5$ |
| $OCH_2COOH$ | $OCH_2COOH$ | OH | $OCH_3$ |
| $OCH_2COOCH_3$ | $OCH_3$ | OH | $OCH(CH_3)COOH$ |
| $OC_2H_4COOH$ | $OC_2H_5$ | \multicolumn{2}{l}{$-O-CH_2-O-$} |
| $OCH_2COOH$ | $OCH_3$ | \multicolumn{2}{l}{$-O-C(COOH)_2-O-$} |
| $OC_2H_4COOH$ | $OC_2H_4COOH$ | \multicolumn{2}{l}{$-O-C(COOCH_3)_2-O-$} |
| $OCH_3$ | $OCH_3$ | | |

TABLE 4

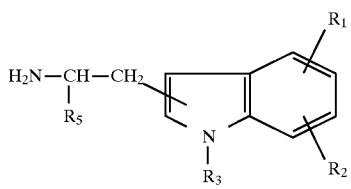

| $R_1^*$ | $R_1$ | $R_1$ | $R_1$ |
|---|---|---|---|
| $OCH_3$ | $OCH_2COOH$ | $OCH_2COOCH_3$ | $OC_2H_4COOH$ |
| $CH_3$ | $COOCH_3$ | $OC_2H_5$ | $O(CH_2)_2CH_3$ |

*the substituent $R_1$ bonds to the 6- or 7-position of the indole nucleus.

The compound of the present invention may be prepared by the following processes.

Process (a):

The compound of the formula [I] of the present invention may be prepared by reacting a compound of the formula [III]:

[III]

wherein $R_4$ is the same as defined above, with a compound of the formula [IV]:

[IV]

wherein $R_1$, $R_2$, $R_3$ and $R_5$ are the same as defined above, or a salt thereof.

The reaction is carried out in a suitable solvent or without a solvent. The solvent should be selected according to the kinds of the starting compounds to be used, and includes, for example, alcohols (e.g. methanol, ethanol, isopropanol, etc.), ketones (e.g. acetone, methyl ethyl ketone, etc.), halogenated hydrocarbons (e.g. methylene chloride, chloroform, etc.), ethers (e.g. diethyl ether, tetrahydrofuran, dioxane, etc.), aromatic hydrocarbons (e.g. benzene, toluene, etc.), ethyl acetate, N,N-dimethylformamide, dimethylsulfoxide, and the like, and these solvents may be used alone or in a combination of two or more thereof. Besides, when the compound [IV] is in the form of an acid addition salt, for example, a salt with an inorganic acid such as hydrochloride, hydrobromide, etc., or a salt with an organic acid such as oxalate, maleate, fumarate, etc., the reaction is carried out in the presence of a base. The base includes, for example, an alkali metal hydrogen carbonate such as sodium hydrogen carbonate, potassium hydrogen carbonate, etc., an alkali metal carbonate such as sodium carbonate, potassium carbonate, etc., or an organic base such as triethylamine, tributylamine, diisopropylethylamine, N-methylmorpholine, etc. Further, when a carboxyl group is included in the substituent $R_1$ or $R_2$, the reaction is carried out in the presence of a base, as mentioned above.

The reaction temperature varies according to the kinds of the starting compounds to be used, but it is usually in the range of from room temperature to about 150° C., preferably in the range of from about 25° C. to about 100° C.

In the process (a), both the starting compounds [III] and [IV] have an asymmetric carbon atom, and the reaction proceeds with keeping the stereo-configuration of the asymmetric carbon atom to give the desired compound [I] having the same stereo-configuration. That is, for example, the desired compound [I] having (R,R)-configuration is obtained from the starting compound [III] having R-configuration and the starting compound [IV] having R-configuration.

The optically active compound of the formula [III] may be prepared, for example, by a similar method to that disclosed in Bloom, J. D. et al., J. Med. Chem., 35, 3081–3084 (1992), or in Eliel, E. L. & Delmonte, D. W., J. Org. Chem., 21, 596–597 (1956). The optically active compound of the formula [IV] may be prepared, for example, by a similar method to that disclosed in Repke, D. B. & Ferguson, W. J., J. Heterocycl., Chem., 13, 775–778 (1976).

The starting compound of the formula [IV] may be prepared, for example, by the method disclosed in J. Org. Chem., 25, 1548–1558 (1960).

Among the starting compounds of the formula [IV], the compound of the formula [IV] wherein the moiety of the following structure:

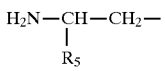

wherein $R_5$ is the same as defined above, bonds to the 3-position of the indole nucleus may be prepared according to the method disclosed in J. Org. Chem., 51, 4294–4295 (1986).

Process (b):

The compound of the formula [I] of the present invention wherein the substituent $R_1$ is a more limited group $R_1'$, i.e. the compound of the formula [I-b]:

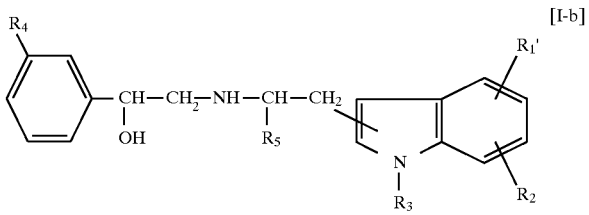

wherein $R_1'$ is a lower alkyl group being optionally substituted by a hydroxy group, a phenylsulfonylamino group, a lower alkylsulfonylamino group, a mono- or di-lower alkylaminosulfonyl group, or a group selected from the following (a)', (b), (c) and (d)', or combines with $R_2$ to form a methylenedioxy group, said methylenedioxy group being optionally substituted by a carboxyl group or a lower alkoxycarbonyl group, (a)' a group of the formula:—X'—Ra (wherein X' is O or S, Ra is the same as defined above, provided that when X' is S, then Ra is a lower alkyl group);

(b) a group of the formula:

$$-[O(CH_2)_m-CH]_n-Rbb$$
$$\phantom{-[O(CH_2)_m-C}|$$
$$\phantom{-[O(CH_2)_m-C}Rb$$

(wherein Rb, Rbb, m and n are the same as defined above);

(c) a group of the formula:—$O(CH_2)_p$—Rc (wherein Rc and p are the same as defined above);

(d)' a group of the formula:—Y'—$(CH_2)_q$—Rd (wherein Y' is S, Rd and q are the same as defined above);

may be prepared by reacting a compound of the formula [V]:

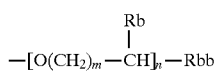

[V]

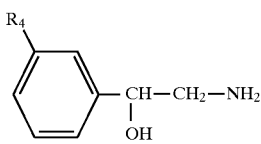

wherein $R^4$ is the same as defined above, with a compound of the formula [VI]:

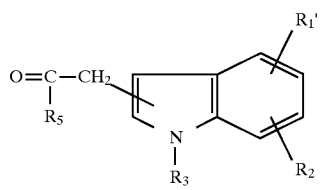

[VI]

wherein $R_1'$, $R_2$, $R_3$ and $R_5$ are the same as defined above, under the reducing conditions.

The "reaction under reducing condition" in the present process means reaction of the compound [V] and the compound [VI] in the presence of a reducing agent or a catalyst which may reduce only the imine moiety formed during the reaction but does not affect the carbonyl group at all.

The reducing agent includes, for example, sodium cyanoborohydride, and the catalyst includes, for example, palladium, platinum oxide, etc.

The reaction is carried out in the presence of a reducing agent or a catalyst in a suitable solvent. The solvent is preferably alcohols such as methanol, ethanol, etc. The reaction is usually carried out at a temperature of from about 20° C. to about 80° C. when a reducing agent is used, and when a catalyst is used, it is usually carried out at a temperature of from about 10° C. to about 25° C.

Process (c):

The compound of the formula [I] wherein a carbonyl group or a cyano group is not included in the substituent $R_1$ or $R_2$, i.e. the compound of the formula [I-c]:

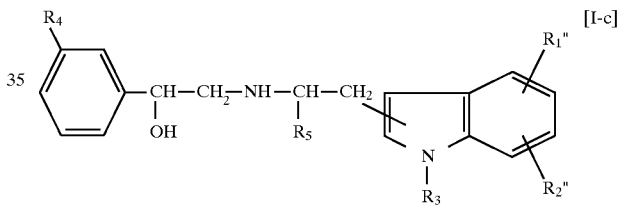

wherein $R_1''$ is a lower alkyl group being optionally substituted by a hydroxy group, a phenylsulfonylamino group, a lower alkylsulfonylamino group, a mono- or di-lower alkylaminosulfonyl group, or a group selected from the following (a) or (c)'', or combines with $R_2''$ to form a methylenedioxy group, (a) a group of the formula:—X—Ra (wherein X and Ra are the same as defined above);

(c)'' a group of the formula:—$O(CH_2)_p$—Rc'' (wherein Rc'' is a hydroxy group, a phenyl group, or a group of the formula:

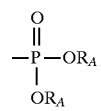

(wherein $R_A$ is a hydrogen atom or a lower alkyl group), and p is the same as defined above), $R_2''$ is a hydrogen atom, a halogen atom, a lower alkyl group being optionally substituted by a hydroxy group, a hydroxy group, a lower alkoxy group, or the group of the above (c)'', or combines with $R_1''$ to form a methylenedioxy group, and $R_3$, $R_4$ and $R_5$ are the same as defined above, may be prepared by subjecting a compound of the formula [VII]:

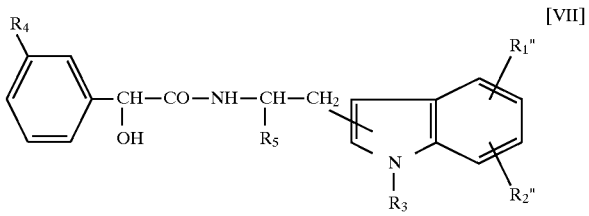

wherein $R_1''$, $R_2''$, $R_3$, $R_4$ and $R_5$ are the same as defined above, to reduction.

The reaction is carried out in the presence of a reducing agent in a suitable solvent. The reducing agent includes, for example, diboran, lithium aluminum hydride, or an alkoxy-complex thereof, a transition metal salt thereof, sodium borohydride appended with aluminum chloride, boron trifluoride, phosphorus oxychloride or a carboxylic acid (e.g. acetic acid, trifluoroacetic acid, etc), etc. The solvent includes, for example, ethers such as diethyl ether, tetrahydrofuran, dimethoxyethane, dioxane, diglyme, etc. The reaction temperature varies according to the kinds of the reducing agent to be used, but it is usually in the range of from about 0° C. to about 160° C.

The stereo-configuration of the asymmetric carbon atom of the starting compound [VII] is remained in the final product in the above process.

The starting compound [VII] is a novel compound, and is prepared, for example, by reacting a compound of the formula [IX]:

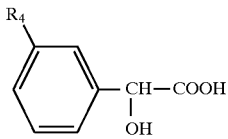

wherein $R_4$ is the same as defined above, with a compound of the formula [X]:

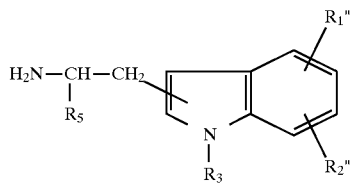

wherein $R_1''$, $R_2''$, $R_3$ and $R_5$ are the same as defined above, or a salt thereof.

The reaction of the compound [IX] and the compound [X] is carried out in the presence of a condensing agent such as N,N'-dicyclohexylcarbodiimide, 1-ethyl-3-(3-dimethylaminopropyl)carbodiimide hydrochloride, N,N'-carbonyldiimidazole, N,N'-carbonyldisuccinimide, 1-ethoxycarbonyl-2-ethoxy-1,2-dihydroquinoline, diphenylphosphoryl azide, propanephosphonic anhydride, etc. When N,N'-dicyclohexylcarbodiimide or 1-ethyl-3-(3-dimethylaminopropyl)carbodiimide hydrochloride is used as a condensing agent, the reaction may be carried out with adding thereto N-hydroxysuccinimide, 1-hydroxybenzotriazole, etc.

The reaction is usually carried out in a suitable solvent. The solvent includes, for example, the same solvents as mentioned for the process (a). Besides, the compound [X] may be used in the form of an acid addition salt thereof as mentioned in the process (a), and when the acid addition salt of the compound [X] is used, the reaction is carried out in the presence of an organic base such as triethylamine, tributylamine, diisopropylethylamine, N-methylmorpholine, etc. The reaction is usually carried out at a temperature of from about 20° C. to about 50° C.

The stereo-configuration of the compound [IX] and the compound [X] is remained in the desired compound [VII].

The optically active compound of the compound [IX] is prepared, for example, by a similar method to that disclosed in Collet, A. and Jacques. J., Bull. Soc. Chim. France, 3330–3334 (1973).

The optically active compound of the compound [IX] is prepared, for example, by a similar method to that disclosed in Japanese Patent First Publication (Kokai) No. 22559/1988.

The products obtained in the above processes can be isolated, and purified by a conventional method such as chromatography, recrystallization, reprecipitation, etc.

The products obtained in the above processes can be obtained either in the form of an acid addition salt thereof or a free base, according to the reaction conditions to be employed. These products may be converted into an acid addition salt or a free base by a conventional method.

In each of the above processes, when the substituent $R_1$ or $R_2$ is an amino group or a lower alkoxy group substituted by a group of the formula:

or when the substituent $R_1$ or $R_2$ contains a carboxyl group or a hydroxy group, the desired compound may be efficiently obtained by reacting the starting compounds wherein said substituent is protected by a conventional protecting group, and then, followed by removing the protecting groups from the products.

When the compounds of the present invention obtained in the above processes or the starting compounds are a racemic compound or in the form of a mixture of diastereomers, each stereoisomer is separated by a conventional method, for example, by the method disclosed in European Patent Publication No. 455006.

BEST MODE FOR CARRYING OUT THE INVENTION

Pharmacological Experiments:

The following pharmacological experiments were done in order to evaluate the activities of the representative compounds of the present invention in terms of:

(1) Human $\beta_3$- and $\beta_2$-adrenergic receptor-stimulating activities (2) Reducing activity of blood glucose level, and (3) Anti-obesity activity.

First, the establishment of the cell lines highly expressing human $\beta_3$- and $\beta_2$-adrenergic receptors is explained, and then, the experiments using thereof are exemplified.

Establishment of the cell line highly expressing human $\beta_3$-adrenergic receptor (1) Construction of expression vector:

An expression vector for animal cells, pKCRH2 [Mishina et al., Nature 307: 604–608 (1984)] was digested with a restriction endonuclease SalI, and was blunted with DNA Blunting Kit (Takara Shuzo Co., Ltd). Separately, another expression vector for animal cells, pSV2-neo [Southern and Berg, J. Mol. Appl. Genet. 1: 327–341 (1982)] was digested with restriction endonucleases AccI and AatII, and blunted with DNA Blunting Kit. These DNAs were ligated with DNA Ligation Kit (Takara Shuzo Co., Ltd.) and were introduced into E. coli HB101 in a conventional manner to give the transformants. Plasmid DNAs were prepared from the transformants and digested with a restriction endonuclease PstI. A clone which produced about 3.8 kbp, 2.2 kbp, 1.4 kbp, and 0.9 kbp fragments was selected to give a plasmid named pKCN0. Plasmid pKCN0 was digested with a restriction endonuclease HindIII and ligated with the following synthetic adaptor 1 represented by SEQ ID NO: 1 by DNA Ligation Kit.

5'-AGCTCCTGCAGGCGCGCCGATATCTCGAGCGGCCGCGGTACCA-3'
3'-GGACGTCCGCGCGGCTATAGAGCTCGCCGGCGCCATGGTTCGA-5'

The reaction mixture was used for transformation of E. coli HB101 and plasmid DNAs were prepared from the selected transformants. The plasmid DNAs were digested with restriction endonucleases DraI and HindIII, and a clone which produced about 430 bp fragment was selected to give a plasmid named pKCN1 for expression vector.

(2) Construction of expression plasmid:

Total RNA was extracted from human neuroblastoma cell line SK-N-MC (ATCC HTB 10), and cDNA was synthesized by using SuperScript Systems (Life Technologies). cDNA was amplified with GeneAmp PCR Kit (Perkin-Elmer) by using the following oligonucleotides 1 and 2 represented by SEQ ID NO: 2 and NO: 3, respectively, for primers. 10% Dimethyl sulfoxide was added to the reaction mixture at the PCR reaction.

5'-CCACCTGCAGGTGATTTGGGAGACCCC-3' oligonucleotide 1

5'-TTCTCGAGCCGGGGAATCCCATGGGAC-3' oligonucleotide 2

After the reaction mixture was digested with restriction endonucleases Sse8387I and StuI, about 1.3 kbp fragment was isolated by electrophoresis. This fragment was ligated with expression vector pKCN1 which was digested with restriction endonucleases Sse8387I and EcoRV, and the resultant was introduced into E. coli HB101 in a conventional manner. Plasmid DNA was prepared from the selected transformant and the nucleotide sequence of the about 1.3 kbp fragment obtained by digestion of the plasmid DNA with restriction endonucleases Sse8387I and XhoI was determined. The sequence was identical with that of human $\beta_3$-adrenergic receptor cDNA reported by Lelias et al. [FEBS Lett. 324: 127–130 (1994)]. This plasmid for expressing human $\beta_3$-adrenergic receptor was named as pKREX10.

(3) Establishment of the highly expressing cell line:

The Chinese hamster ovary cell line CHO-K1 (ATCC CCL 61) was transformed with the plasmid pKREX10 expressing human $\beta_3$-adrenergic receptor by calcium phosphate method, and transformants were selected with 600 µg/ml of G-418 (Life Technologies) in MEM-Dulbecco's medium (ICN Biomedicals) supplemented with 10% fetal bovine serum and 11.5 µg/ml proline. In the cultures of 69 G-418 resistant clones, these cells were peeled off by incubation with phosphate-buffered saline containing 0.5 mM ethylenediaminetetraacetate (EDTA) at 37° C. for 10 minutes after the medium was removed. The cells were collected by centrifugation and suspended in 10 mM Tris-HCl buffer (pH 7.5) containing 1 mM EDTA at the concentration of $5 \times 10^6$ cells/ml. This suspension (20 µl) and (-)3-[$^{125}$I]iodocyanopindolol (1.5 nM) (Amersham) were mixed in RPMI-1640 medium (200 µl) (ICN Biomedicals) containing 1% bovine serum albumin, 0.1% $NaN_3$ and 20 mM HEPES buffer (pH 7.4), and the mixture was incubated at 4° C. for 2 hours. The reaction mixture was filtered with glass filter GF/C (Whatman) presoaked with 0.3% polyethyleneimine and washed by using BIO-DOT apparatus (Bio-Rad Laboratories), and the radioactivity on the filter was counted by γ-ray counter. One clone named CHO/pKREX10-36, which showed the highest radioactivity, was used for human $\beta_3$-adrenergic receptor-expressing cell line. Establishment of the cell line highly expressing human $\beta_2$-adrenergic receptor cDNA was synthesized with Poly(A)$^+$RNA derived from human brain (Clontech: trade number; CL6516-1) by using SuperScript Systems (Life Technologies). This cDNA was amplified with GeneAmp PCR Kit (Perkin-Elmer) by using the following oligonucleotides 3 and 4 represented by SEQ ID NO: 4 and NO: 5, respectively, for primers.

5'-ACACCTGCAGGTGAGGCTTCCAGG-
   CGTCC-3'         oligonucleotide 3

5'-TGTAAGCTTCTGCTTTACAGCAGT-
   GAGTC-3'         oligonucleotide 4

After the reaction mixture was digested with restriction endonucleases Sse8387I and HindIII, about 1.4 kbp fragment was isolated by electrophoresis. This fragment was ligated with expression vector pKCN1 digested with restriction endonucleases Sse8387I and HindIII, and was introduced into E. coli HB101 in a conventional manner. Plasmid DNA was prepared from the selected transformant, and the nucleotide sequence of the about 1.4 kbp fragment obtained by digestion of this plasmid DNA with restriction endonucleases Sse8387I and HindIII was determined. The sequence was identical with that of human $\beta_2$-adrenergic receptor cDNA reported by Kobilka B. K. et al. [Proc. Natl. Acad. Sci U.S.A. 84: 46–50 (1987)]. This plasmid was named as pKREX21 for highly expressing human $\beta_2$-adrenergic receptor, and was introduced into CHO-K1 in the same manner as the method of establishment of the cell line highly expressing human $\beta_3$-adrenergic receptor. One clone named CHO/pKREX21-8, which showed highest radioactivity, was used for human $\beta_2$-adrenergic receptor-expressing cell line.

Experiment 1 Human β-adrenergic receptor-stimulating activity:

Human $\beta_3$-adrenergic receptor-highly expressing cell line CHO/pKREX10-36 was cultured for 3 days with MEM-Dulbecco's medium supplemented with 10% fetal bovine serum, 11.5 µg/ml proline and 200 µg/ml G-418. The cells were peeled off by incubation with phosphate-buffered saline containing 0.5 mM EDTA at 37° C. for 10 minutes after the medium was removed. The CHO/pKREX10-36 cells were collected by centrifugation, and suspended in Hanks' balanced salts (ICN Biomedicals) containing 1 mM L-ascorbic acid and 1 mM 3-isobutyl-1-methylxanthine at the concentration of about $2 \times 10^6$ cells/ml. This suspension (100µl) and a test compound were mixed in the same balanced salt (500 µl) and incubated at 37° C. for 30 minutes, followed by boiling for 5 minutes to terminate the reaction. After centrifugation of the reaction mixture, the amount of cAMP in the supernatant was measured by using cAMP EIA System (Amersham).

Similarly, the amount of cAMP was measured by using CHO/pKREX21-8 for highly expressing human $\beta_2$-adrenergic receptor instead of the CHO/pKREX10-36 for highly expressing human $\beta_3$-adrenergic receptor.

The amounts of cAMP when adding $10^{-5}$M of (-)-isoproterenol to the reaction mixture or not adding thereof at all were estimated as 100% and 0%, respectively, and the relative maximal response of each compound of the present invention is expressed as intrinsic activity % [I.A. (%)].

$EC_{50}$ value which is a concentration of the test compound to be required to achieve 50% of cAMP accumulation was calculated by least squares regression analysis of concentration-response curve of each compound.

The results are shown in Table 5. The above mentioned Compounds A, B and C were used as a reference compound.

TABLE 5

| Test comp. | Human $\beta_3$- and $\beta_2$-adrenergic receptor-stimulating activity | | | | |
|---|---|---|---|---|---|
| | $EC_{50}$ value (nM) | | Ratio of | I.A. value (%) | |
| | $\beta_3$-receptor | $\beta_2$-receptor | $\beta_2/\beta_3$ | $\beta_3$-receptor | $\beta_2$-receptor |
| 1*[1] | 1.7 | 25 | 14.7 | 113 | 33 |
| 1-A | 0.67 | 13 | 19.4 | 114 | 36 |
| 1-A-b | 0.36 | 3.6 | 10.0 | 89 | 35 |
| 2 | 2.0 | 55 | 27.5 | 117 | 31 |
| 2-A | 0.96 | 15 | 15.6 | 96 | 23 |
| 3 | 22 | 170 | 7.7 | 102 | 22 |
| 4 | 16 | 43 | 2.7 | 116 | 36 |
| 5 | 12 | 33 | 2.8 | 95 | 41 |
| 6 | 35 | 88 | 2.5 | 91 | 19 |
| 7 | 25 | 33 | 1.3 | 76 | 15 |
| 8 | 31 | —*[2] | — | 92 | 5 |
| 12 | 4.0 | 31 | 7.8 | 98 | 13 |
| 13 | 31 | —*[2] | — | 101 | 6 |
| 14 | 0.43 | 6.0 | 14.0 | 95 | 29 |
| Comp. A | 910 | 410 | 0.5 | 92 | 16 |
| Comp. B | 180 | —*[2] | — | 100 | 8 |
| Comp. C | 540 | —*[2] | — | 105 | 5 |
| IP*[3] | 5.5 | 5.6 | 1.0 | 100 | 100 |

*[1]The compound of Example 1 (hereinafter, the same)
*[2]No-detective because the activity of these compounds was quite weak.
*[3](-)-Isoproterenol A compound having a low $EC_{50}$ value and a high I.A. value is considered to have a potent human $\beta_3$- or $\beta_2$-adrenergic receptor-stimulating activity. Thus, as shown in Table 5, the compounds of the present invention, especially the compounds of Example 1, 1-A, 1-A-b, 2, 2-A and 14 are proved to have a potent stimulating activity of human $\beta_3$-adrenergic receptor. Besides, human $\beta_3$-adrenergic receptor-stimulating activity of the present compounds are stronger than human $\beta_2$-adrenergic receptor- stimulating activity thereof. Particularly, the compounds of Example 1, 1-A, 1-A-b, 2, 2-A and 14 have excellent adrenoceptor selectivity for human $\beta_3$ -adrenergic receptor.

On the other hand, the reference Compounds A, B and C as mentioned hereinbefore showed quite weak human $\beta_3$-adrenergic receptor-stimulating activity as compared with the compounds of the present invention.

Besides, when studying in terms of increasing activity of the rate of spontaneous contraction in isolated ginea pig right atrium, the compounds of the present invention hardly showed human $\beta_1$-adrenergic receptor-stimulating activity.

As is shown in the above results, the compounds of the present invention can be human $\beta_3$-adrenergic receptor-stimulating agent with excellent adrenoceptor selectivity.

Experiment 2 Blood glucose reducing activity on fasted mouse:

A test compound suspended in 0.5% tragacanth solution was orally administered to a ddY male mouse (weight: 20–30 g) under being fasted, and the blood was collected before and at three hours after the administration of the test compound. The glucose level in the blood was determined by the method of Kunst A., et al. (Hexokinase/G6PDH method) [Bergmeyer, H. U. (eds.), Methods in Enzymology, vol. VI, 3rd edition, Verlag Chemie GmbH, Weinheim·Deerfield Beach, Florida·Basel, 163–172 (1984)]. The blood glucose reducing activity of the test compound was expressed by $ED_{25}$ value which is a concentration of the test compound required to reduce the glucose level in blood before the administration of the test compound by 25%. Gliclazide was used as a reference compound which is a commercially available drug for treatment of diabetes mellitus. The results are shown in Table 6.

TABLE 6

| Test compound | Blood glucose reducing activity in mice ($ED_{25}$; mg/kg po) |
|---|---|
| 1* | 0.05 |
| 1-A | 0.003 |
| 2 | 0.03 |
| 3 | 3.3 |
| 5 | 4.5 |
| 6 | 4.5 |
| 7 | 1.5 |
| 8 | 1.4 |
| 10 | 0.1 |
| Gliclazide | 0.87 |

*The compound of Example 1 (hereafter, the same)

Experiment 3 Anti-obesity activity on diabetic obese mouse:

A test compound suspended in 0.5% tragacanth solution was orally administrated to a diabetic obese mouse (KK-Ay/Ta, Jcl. female; 50–60 g, Clea Japan Inc.) at a dose of 3 mg/kg/day for three weeks, and then, the retroperitoneal adipose tissue and the interscapular adipose tissue were taken, and the weights thereof were measured as white adipose tissue and brown adipose tissue, respectively. The results are shown in Table 7.

TABLE 7

| Group | Weight of white adipose tissue (g) | Weight of brown adipose tissue (g) |
|---|---|---|
| Control | 4.92 ± 0.28 | 0.460 ± 0.03 |
| Compound of Example 1 | 2.35 ± 0.12* | 0.289 ± 0.04* |

*It is significantly different from the data of the control with $p < 0.01$.

The compounds of the present invention show low toxicity, for example, the compound of Example 1-A showed no toxicity at all by oral administration at a dose of 300 mg/kg (weight) in acute toxicity experiment using mice. Thus, when taking into consideration the therapeutically effective dose, the compounds of the present invention have no problem in safety to living body.

The compounds of the present invention are excellent $\beta_3$-adrenergic receptor-stimulating agents with high adrenoceptor selectivity, and are useful in the prophylaxis or treatment of obesity and diabetes mellitus in mammals including human beings. Besides, the compounds of the present invention can also be used in the treatment of irritable bowel syndrome, acute or chronic diarrhea, or in the improvement of symptoms such as abdominal pain, nausea, vomiting, abdominal discomfort, etc., accompanied by peptic ulcer, acute or chronic gastritis, biliary dyskinesia, cholecystitis, etc.

The compounds [I] of the present invention or a pharmaceutically acceptable salt thereof can be administered as β₃-adrenergic receptor-stimulating agent either orally, parenterally or rectally, but preferably by oral route. The dose of the compounds of the present invention varies according to the administration route, the conditions, ages of the patients, or kinds of objects (prophylaxis or treatment), etc., but is usually in the range of 0.01–20 mg/kg/day, preferably in the range of 0.05–10 mg/kg/day.

The compounds of the present invention is usually administered in the form of a pharmaceutical preparation which is prepared by mixing thereof with a pharmaceutically acceptable carrier or diluent. The pharmaceutically acceptable carrier or diluent may be any conventional ones which are usually used in the pharmaceutical field, and do not react with the compounds of the present invention. Suitable examples of the pharmaceutically acceptable carrier or diluent are, for example, lactose, glucose, mannitol, dextrin, starch, white sugar, magnesium metasilicate aluminate, synthetic aluminum silicate, crystalline cellulose, sodium carboxymethylcellulose, hydroxypropyl starch, calcium carboxylmethylcellulose, ion exchange resin, methylcellulose, gelatin, gum arabic, hydroxypropyl cellulose, low substituted hydroxypropyl cellulose, hydropropylmethylcellulose, polyvinylpyrrolidone, polyvinyl alcohol, light anhydrous silicic acid, magnesium stearate, talc, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, nonionic surfactant, propyleneglycol, water, etc.

The pharmaceutical preparation is, for example, tablets, capsules, granules, powders, syrups, suspensions, suppositories, gel preparations, injection preparations, etc. These preparations may be prepared by a conventional method. In the preparation of liquids, the compound of the present invention is dissolved or suspended in water or a suitable other solvent, when administered. Tables and granules may be coated by a conventional method. In the injection preparations, it is preferable to dissolve a pharmaceutically acceptable acid addition salt of the compound [I] of the present invention in water, but if necessary, it may be dissolved in an isotonic agent, and further, a pH adjustor, a buffering agent or a preservative may be added thereto.

These preparations may contain the compound of the present invention at a ratio of at least 0.01%, preferably at a ratio of 0.05–70%. These preparations may also contain other pharmaceutically effective compounds as well.

EXAMPLES

The present invention is illustrated in more detail by the following Reference Examples and Examples, but should not be construed to be limited thereto.

The identification of the compounds are carried out by Elementary analysis, Mass spectrum, IR spectrum, NMR spectrum, etc.

The following abbreviations may be used in the present description in order to simplify the disclosure.

Me: Methyl
Et: Ethyl
Ph: Phenyl
E: Ethanol
M: Methanol
H: n-Hexane
DE: Diethyl ether
CF: Chloroform
EA: Ethyl acetate
DMF: Dimethylformamide
s: Singlet
d: Doublet
dt: Double triplet
dd: Double doublet
t: Triplet
m: Multiplet
q: Quartet
MS: Mass spectrum Reference Example 1

Preparation of 3-(2-aminopropyl)-7-methoxyindole:

The title compound is prepared by the following processes according to the method disclosed in British Patent Publication No. 974,893.

(1) Dimethylformamide (DMF, 16 ml) is cooled in an ice bath, and thereto is added dropwise phosphorus oxychloride (5 ml), and the mixture is stirred for 10 minutes. A solution of 7-methoxyindole (6.5 g), which is prepared from 3-methyl-2-nitroanisole according to the method disclosed in Heterocycles, 16, 1119–1124 (1981), in DMF (16 ml) is added dropwise to the mixture, and the mixture is stirred at room temperature for two hours. To the mixture is added 30% aqueous sodium hydroxide solution (30 ml) under ice-cooling, and the mixture is heated at about 80° C. for five minutes in a hot bath, and allowed to stand to cool. The precipitates are collected by filtration, washed with water, and dried to give crude 7-methoxyindol-3-aldehyde (4.6 g).

(2) A mixture of ammonium acetate (3.6 g), acetic anhydride (1 ml) and acetic acid (3.2 ml) is heated with stirring at 50° C. for 20 minutes, and thereto are added the product (4.5 g) obtained in the above (1), acetic acid (19.2 ml) and nitroethane (16 ml). The mixture is heated to 100° C., and thereto is added sodium acetate (2.25 g). The mixture is refluxed for two hours while acetic anhydride (3.2 ml) is gradually added dropwise thereto. After allowed to stand to cool, water is added to the mixture, and the precipitated solid is collected by filtration, washed with water, and dried to give crude 1-(7-methoxyindol-3-yl)-2-nitropropene (3.35 g).

(3) A solution of the nitropropene compound (3.2 g) obtained in the above (2) in tetrahydrofuran (60 ml) is added dropwise to a suspension of lithium aluminum hydride (3.2 g) in diethyl ether (60 ml) under ice-cooling, and the mixture is refluxed for 5.5 hours. A saturated aqueous solution of sodium potassium tartrate is added to the mixture under ice-cooling, and the insoluble materials are removed by filtration, and the filtrate is dried over anhydrous magnesium sulfate. The mixture is evaporated to remove the solvent under reduced pressure to give the crude desired compound (3.2 g) as an oily product, which is used as the starting compound in Example 1.

MS (m/z):205 (MH⁺)

Reference Example 2

Preparation of 3-(2-aminopropyl)-6-methoxycarbonylmethoxyindole:

(1) 6-Hydroxyindole (2.9 g), methyl chloroacetate (2.7 g), potassium carbonate (5.5 g) and potassium iodide (0.2 g) are added to acetone (100 ml), and the mixture is refluxed for 8 hours. The reaction mixture is cooled to room temperature, and the insoluble materials are removed by filtration. The filtrate is evaporated under reduced pressure. The residue is purified by silica gel column chromatography (eluent; chloroform) to give 6-methoxycarbonylmethoxyindole (2.83 g).

¹H-NMR spectrum (CDCl₃):3.78(3H,s,COOCH₃),4.67 (2H,s,OCH₂), 6.49(1H,m),6.83(1H,m),6.88(1H,s),7.11(1H,m),7.53(1H,m),8.2(1H,s,NH)

(2) To a solution of the above product (2.77 g) in benzene (50 ml) is added a solution of 2-nitropropene (3.56 g) in benzene (17.8 ml), and the mixture is refluxed for 15 hours. The mixture is evaporated to remove the solvent under reduced pressure, and the residue is purified by silica gel column chromatography (eluent; chloroform) to give 3-(2-nitropropyl)-6-methoxycarbonylmethoxyindole (2.15 g) as an oily product.

¹H-NMR spectrum (CDCl₃):1.56(3H,d,J=7 Hz,CHC$\underline{H}_3$),3.10–3.48(2H, m, C$\underline{H}_2$CHNO₂),3.77(3H,s,COOCH₃),4.64(2H,s,OCH₂),4.92(1H,m,C$\underline{H}$NO₂),6.76–7.05(3H,m),7.48(1H,m),8.08(1H,s,NH)

(3) The above product (2.1 g) is dissolved in ethanol (50 ml), and thereto is added Raney-nickel, and the mixture is subjected to reduction at 50° C. under atmospheric pressure. After the theoretical amount of hydrogen is consumed, the Raney-nickel is removed by filtration. The filtrate is evaporated to remove the solvent to give crude 3-(2-aminopropyl)-6-methoxycarbonylmethoxyindole (1.98 g) as an oily product, which is used as the starting compound in Example 7.

MS (m/z):263(MH⁺)

Reference Examples 3–13

In the same manner as in Reference Example 1 or 2, the following starting compounds as listed in Table 8 are obtained.

TABLE 8

$$H_2N-CH-CH_2-\text{[indole with }R_1, R_2\text{]}$$
$$|$$
$$CH_3$$

| Ref. Ex. | R₁ | R₂ | MS (m/z) (MH⁺) | Process |
|---|---|---|---|---|
| 3 | 7-OC₂H₅ | H | 219 | 1*¹ |
| 4 | 6-OCH₃ | H | 205 | 1 |
| 5 | 7-OCH₂Ph | H | 281 | 1 |
| 6 | 6-CH₃ | H | 189 | 1 |
| 7 | 7-CH₃ | H | 189 | 1 |
| 8 | 6-COOCH₃ | H | 233 | 2*² |
| 9 | 4-OCH₃ | H | 205 | 1 |
| 10 | 4-CH₃ | H | 189 | 1 |
| 11 | 6-SO₂N(CH₃)₂ | H | 281 | 2 |
| 12 | 6-OCH₃ | 7-OCH₃ | 219 | 1 |
| 13 | 7-OCH₂COOCH₃ | H | 63 | 2 |

*¹Prepared in the same manner as in Reference Example 1.
*¹Prepared in the same manner as in Reference Example 2.

Example 1

Preparation of 2-[3-(7-methoxyindol-3-yl)-2-propylamino]-1-(3-chlorophenyl)ethanol:

Process (a):

To methanol (20 ml) are added (3-chlorophenyl)oxirane (0.77 g) and 3-(2-aminopropyl)-7-methoxyindole (2.16 g), and the mixture is stirred at room temperature for 64 hours. The mixture is evaporated to remove the solvent under reduced pressure, and the residue is purified by silica gel column chromatography (eluent; chloroform/methanol=12:1), and the fractions containing the desired product are combined and concentrated under reduced pressure to give the oily product (1.06 g).

¹H-NMR spectrum (CDCl₃): 1.12(3H,d,J=7 Hz, CHC$\underline{H}_3$), 2.61 (1H,m), 2.78–2.86(2H,m),2.88–3.12(2H,m),3.95 (3H,s,OCH₃),4.56(1H,m,C$\underline{H}$OH) 6.65(1H,m),6.93–7.09 (2H,m),7.11–7.29(4H,m),7.33(1H,m),8.25(1H,s, indole-NH)

The above oily product (0.3 g) is treated with fumaric acid to give a fumarate of the desired compound (0.15 g) (the fumarate of the compound of Example 1).

M.p. 143°–147° C. (recrystallized from ethanol/diethyl ether)

Process (b):

To methanol (10 ml) are added 7-methoxyindol-3-acetone (0.4 g), which is prepared by the method disclosed in British Patent No. 974,893, and 2-(3-chlorophenyl)ethanolamine hydrochloride (0.45 g), and sodium cyanoborohydride (0.2 g) is added thereto under ice-cooling. The mixture is stirred for five minutes, and then, stirred at room temperature for 18 hours. The mixture is evaporated to remove the solvent under reduced pressure, and to the residue is added a saturated aqueous sodium hydrogen carbonate solution. The mixture is extracted with ethyl acetate, and the extract is washed successively with water and a saturated aqueous sodium chloride solution, and dried over magnesium sulfate. The resultant is evaporated to remove the solvent under reduced pressure, and the resulting residue is purified by silica gel column chromatography (eluent; chloroform/methanol=15:1) to give the desired compound (0.58 g) as an oily product.

Process (c):

(1) To a DMF solution (80 ml) containing 3-(2-aminopropyl)-7-methoxyindole (12.24 g) and 3-chloromandelic acid (7.46 g) is added benzotriazole-N-oxytris(dimethylamino)phosphonium hexafluorophosphate (17.68 g), and then thereto is added dropwise triethylamine (9.8 ml). The mixture is stirred at room temperature for five hours, and to the reaction mixture is added ethyl acetate. The mixture is washed successively with water, 10% aqueous citric acid solution, water, a saturated aqueous sodium hydrogen carbonate solution, water and a saturated aqueous sodium chloride solution, and dried over anhydrous magnesium sulfate. The mixture is evaporated to remove the solvent under reduced pressure, and the residue is purified by silica gel column chromatography (eluent; ethyl acetate/n-hexane=1:1→2:1) to give N-[3-(7-methoxyindol-3-yl)-2-propyl]-3-chloromandelamide (14.02 g) as an oily product.

¹H-NMR spectrum (CDCl₃):1.12, 1.18(3H,d,J=7 Hz,CHC$\underline{H}_3$),2.82– 2.95(2H,m,C$\underline{H}_2$CH),3.97(3H,s,OCH₃), 4.33(1H,m,C$\underline{H}$CH₃),4.85(1H,s,C$\underline{H}$OH), 6.65 (1H,m), 6.86–7.37(7H,m),8.26(1H,d,J=13Hz,CONH)

(2) A solution of the above amide compound (13.4 g) in tetrahydrofuran (144 ml) is added dropwise to a 1M boran-tetrahydrofuran complex solution (144 ml) at 20° C., and the mixture is refluxed for four hours. To the mixture is added dropwise methanol (150 ml) under ice-cooling. The mixture is refluxed for one hour to decompose the excess boran. The mixture is evaporated to remove the solvent under reduced pressure. To the residue is added chloroform, and the mixture is washed successively with a saturated aqueous sodium hydrogen carbonate solution and a saturated aqueous sodium chloride solution, and dried over anhydrous magnesium sulfate. The mixture is evaporated to remove the solvent under reduced pressure, and the residue is purified by silica gel column chromatography (eluent; chloroform/methanol=20:1→10:1) to give the desired compound (7.35 g) as an oily product.

Example 1-A

Preparation of 2-[3-(7-methoxyindol-3-yl)-2-propylamino]-(1R)-1-(3-chlorophenyl)ethanol:

By using (R)-(3-chlorophenyl)oxirane (manufactured by SEPRACO, Ltd.; optical purity: 99.2% e.e.) instead of (3-chlorophenyl)oxirane in Example 1, the desired compound is obtained in the same manner as in Example 1, Process (a) as an oily product.

MS (m/z):359(MH$^+$)

Example 1-A-a and -b

Preparation of 2-[(2R or 2S)-3-(7-methoxyindol-3-yl)-2-propylamino]-(1R)-1-(3-chlorophenyl)ethanol and 2-[(2S or 2R)-3-(7-methoxyindol-3-yl)-2-propylamino]-(1R)-1-(3-chlorophenyl)ethanol:

2-[3-(7-Methoxyindol-3-yl)-2-propylamino]-(1R)-1-(3-chlorophenyl)ethanol (3.0 g) obtained in Example 1-A, which is a mixture of two diastereomers, is separated by column chromatography to give the compound (1-A-a) (0.82 g) eluting with a less polar solvent, and the compound (1-A-b) (1.12 g) eluting with a higher polar solvent.

Compound (1-A-a):

Retention time of high performance liquid chromatography (HPLC): 20.3 min. (optical purity:>99% d.e.)

Separation Condition for HPLC:
1. Column; CHIRALPAK AD (4.6 mmØ×250 mm, Daicel Chemical Industries, Ltd.)
2. Eluent; n-Hexane/ethanol/diethylamine=85:15:0.1
3. Flow rate; 0.4 m/min.
4. Temperature; 40° C.
5. Wave length for detection; 254 nm M.p. 129°–130° C. (recrystallized from ethyl acetate/n-hexane);

$^1$H-NMR spectrum (CDCl$_3$):1.12(3H,t,J=7 Hz,CHCH$_3$),2.57(1H,dd,J=12,7 Hz),2.81(2H,d,J=7 Hz, CH$_2$CH),2.91–3.09(2H,m),3.95(3H,s,OCH$_3$),4.59 (1H,dd,J=8,4 Hz,CHOH),6.64(1H,d,J=8 Hz),6.95(1H,d,J=2 Hz),7.03 (1H,t,J=8 Hz),7.10–7.24(4H,m),7.32(1H,m),8.25(1H,s,indole-NH)

M.p. 86°–87° C. (recrystallized from ethyl acetate/n-hexane);

$^1$H-NMR spectrum (CDCl$_3$):1.12(3H,d,J=7 Hz,CHCH$_3$),2.62(1H,dd, J=12,9 Hz),2.82(2H,d,J=7 Hz,CH$_2$CH),2.87(1H,dd,J=12,4 Hz),3.05(1H,m,CHCH$_3$),3.96(3H,s,OCH$_3$),4.49(1H,dd,J=9,4 Hz,CHOH),6.65(1H,d,J=8 Hz),6.99(1H,d,J=2 Hz),7.04(1H,t,J=8 Hz),7.12–7.25(4H,m),7.33(8.26(1H,s,indole-NH)

Example 2

Preparation of 2-[3-(7-ethoxyindol-3-yl)-2-propylamino]-1-(3-chlorophenyl)ethanol:

(3-Chlorophenyl)oxirane (0.92 g) and 3-(2-aminopropyl)-7-ethoxyindole (2.18 g) are treated in the same manner as in Example 1, Process (a) to give the desired compound (1.16 g) as an oily product.

$^1$H-NMR spectrum (CDCl$_3$):1.12(3H,d,J=6 Hz, CHCH$_3$),1.48(3H,t, J=7 Hz, CH$_2$CH$_3$), 2.4(2H,br,NH,OH),2.60 (1H,d,t,J=12,8 Hz),2.77–2.96 (3H,m),3.04(1H,m),4.20(2H,q,J=7 Hz,CH$_2$CH$_3$),4.55(1H,dd,J=9,4 Hz,CHOH),6.63 (1H, d,J=7 Hz),6.91–7.06(2H,m),7.10–7.25(4H,m),7.32(1H,m ) 8.27(1H,s,indole-NH)

Example 2-A

Preparation of 2-[3-(7-ethoxyindol-3-yl)-2-propylamino]-(1R)-1-(3-chlorophenyl)ethanol:

(R)-(3-Chlorophenyl)oxirane and 3-(2-aminopropyl)-7-ethoxyindole obtained in the above Reference Example 3 are treated in the same manner as in Example 1-A to give the desired compound as oil product.

MS (m/z):373(MH$^+$)

Examples 3–12

Using the corresponding indole compounds obtained in Reference Examples 2 and 4–12 instead of 3-(2-aminopropyl)-7-methoxyindole in Example 1, the compounds as listed in Table 9 are obtained in the same manner as in Example 1, Process (a).

TABLE 9

[Structure: 3-chlorophenyl-CH(OH)-CH$_2$-NH-CH(CH$_3$)-CH$_2$-indole with N-CH$_3$ and R$_1$, R$_2$ substituents]

| Ex. | R$_1$ | R$_2$ | Acid addition Salt | M.p. (°C.) | Solv. for recrystal. | MS (m/z) (MH$^+$) |
|---|---|---|---|---|---|---|
| 3 | 6-OCH$_3$ | H | | Oil | | 359 |
| 4 | 7-OCH$_2$Ph | H | | Oil | | 435 |
| 5 | 6-CH$_3$ | H | — | 103–107 | CF/M | 343 |
| 6 | 7-CH$_3$ | H | — | 97–104 | DE/H | 343 |
| 7 | 6-OCH$_2$-COOCH$_3$ | H | 3/4 HCl. 1/2 H$_2$O | 55–65 | CF/DE | 417 |
| 8 | 6-COOCH$_3$ | H | — | 118–123 | EA/H | 387 |
| 9 | 4-OCH$_3$ | H | | Oil | | 359 |
| 10 | 4-CH$_3$ | H | — | 134–139 | DE/H | 343 |
| 11 | 6-SO$_2$N—(CH$_3$)$_2$ | H | 3/4 HCl. 1/2 H$_2$O | 109–114 | E/DE | 436 |
| 12 | 6-OCH$_3$ | 7-OCH$_3$ | 1/2 Fumarate | 203–207 | E/DE | 389 |

Compound (1-A-b):

Retention time of HPLC: 24.5 min. (optical purity:>99% d.e.)

Separation Condition for HPLC: The same as those in Compound (1-A-a)

Example 13

Preparation of 2-[3-(6-carboxymethoxyindol-3-yl)-2-propylamino]-1-(3-chlorophenyl)ethanol sodium salt:

The compound of Example 7 (0.42 g) and sodium hydroxide (0.3 g) are added to an aqueous methanol solution (methanol/water=2:1,9 ml), and the mixture is refluxed for four hours. Subsequently, the mixture is allowed to stand at 0° C. for two hours, and the precipitated crystals are collected by filtration to give the desired compound (0.24 g) as ½ hydrate.

M.p. 236°–242° C.

Example 14

Preparation of 2-[3-(7-methoxycarbonylmethoxyindol-3-yl)-2-propylamino]-(1R)-1-(3-chlorophenyl)ethanol:

(R)-(3-Chlorophenyl)oxirane and the 3-(2-aminopropyl)-7-methoxycarbonylmethoxyindole obtained in Reference Example 13 are treated in the same manner as in Example 1-A to give the desired compound as an oily product.

MS (m/z):417(MH$^+$)

$^1$H-NMR spectrum (CDCl$_3$):1.13(3H,d,J=6 Hz,CHC$\underline{H}_3$),2.62(1H,dt, J=12,8 Hz),2.77–3.13(4H,m),3.81(3H,s,CO$_2$CH$_3$),4.47–4.68(1H,m,C$\underline{H}$OH),4.75(2H,s,OCH$_2$),6.57(1H d,J=8 Hz),6.92–7.06(2H,m),7.11–7.36(5H,m),8.77(1H,s,indole-NH)

Example 15

Preparation of 2-[3-(7-carboxymethoxyindol-3-yl)-2-propylamino]-(1R)-1-(3-chlorophenyl)ethanol:

The compound obtained in Example 14 and sodium hydroxide are added to an aqueous methanol solution (methanol/water=2:1), and the mixture is treated in the same manner as in Example 13 to give the desired compound.

MS (m/z):403(MH$^+$)

Example 16 (Preparation of tablets)

The following components are mixed and kneaded in a conventional manner, and the mixture is granulated, and the resultants are further compressed for tabletting to give 1,000 tablets (each 100 mg).

| | |
|---|---|
| The compound of Example 1 | 5 g |
| Corn starch | 25 g |
| Lactose | 54 g |
| Crystalline cellulose | 11 g |
| Hydroxypropylcellulose | 3 g |
| Light anhydrous silicic acid | 1 g |
| Magnesium stearate | 1 g |

INDUSTRIAL APPLICATION

The compounds of the present invention are useful as a medicament for mammals including human beings, especially as a $\beta_3$-adrenergic receptor-stimulating agent, and can be used in the treatment of diabetes mellitus and obesity.

We claim:

1. An indole derivative of the formula [I]:

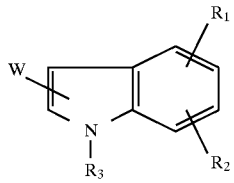

[I]

wherein $R_1$ is a lower alkyl group being optionally substituted by a hydroxy group, a phenylsulfonylamino group, a lower alkylsulfonylamino group, a mono- or di-lower alkylaminosulfonyl group, or a group selected from the following (a) to (d), or combines with $R_2$ to form a methylenedioxy group, said methylenedioxy group being optionally substituted by a carboxyl group or a lower alkoxycarbonyl group, (a) a group of the formula:—X—Ra (wherein X is O, S or NH, Ra is a hydrogen atom or a lower alkyl group, provided that when X is S, then Ra is a lower alkyl group);

(b) a group of the formula:

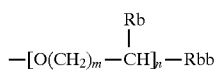

Rb (wherein Rb is a hydrogen atom, a lower alkyl group, a lower alkoxycarbonyl group or a carboxyl group, Rbb is a lower alkoxycarbonyl group or a carboxyl group, m is an integer of 0 to 3, and n is 0 or 1);

(c) a group of the formula:—O(CH$_2$)$_p$—Rc (wherein Rc is a lower alkanoyl group, a hydroxy group, a cyano group, a phenyl group, a mono- or di-lower alkylaminocarbonyl group, or a group of the formula:

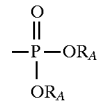

(wherein $R_A$ is a hydrogen atom or a lower alkyl group), and p is an integer of 1 to 4); and (d) a group of the formula:—Y—(CH$_2$)$_q$—Rd (wherein Y is NH or S, Rd is a carboxyl group or a lower alkoxycarbonyl group, and q is an integer of 1 to 4);

$R_2$ is a hydrogen atom, a halogen atom, a lower alkyl group being optionally substituted by a hydroxy group, a hydroxy group, a lower alkoxy group, or a group of the above (b) or (c), or combines with $R_1$ to form a methylenedioxy group, said methylenedioxy group being optionally substituted by a carboxyl group or a lower alkoxycarbonyl group;

$R_3$ is a hydrogen atom or a lower alkyl group;

W is a group of the formula [II] which bonds to the 2- or 3-position of the indole nucleus:

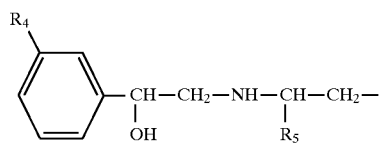

[II]

wherein $R_4$ is a halogen atom or a trifluoromethyl group, and $R_5$ is a lower alkyl group, or a salt thereof.

2. An indole derivative of the formula I-a:

$$R_4-C_6H_4-CH(OH)-CH_2-NH-CH(R_5)-CH_2-\text{[indole with }R_1, R_2, R_3\text{]}$$  I-a wherein $R_1$ is a lower alkyl group being optionally substituted by a hydroxy group, a phenylsulfonylamino group, a lower alkylsulfonylamino group, a mono- or di-lower alkylaminosulfonyl group, or a group selected from the following (a) to (d), or combines with $R_2$ to form a methylenedioxy group, said methylenedioxy group being optionally substituted by a carboxyl group or a lower alkoxycarbonyl group, (a) a group of the formula:—X—Ra, wherein X is O, S or NH, Ra is a hydrogen atom or a lower alkyl group, provided that when X is S, then Ra is a lower alkyl group;

(b) a group of the formula:

$$-\{O(CH_2)_m-CH\}_n-Rbb$$
$$\qquad\qquad\;|$$
$$\qquad\qquad Rb$$

wherein Rb is a hydrogen atom, a lower alkyl group, a lower alkoxycarbonyl group or a carboxyl group, Rbb is a lower alkoxycarbonyl group or a carboxyl group, m is an integer of 0 to 3, and n is 0 or 1;

(c) a group of the formula:—O(CH$_2$)$_p$—Rc, wherein Rc is a lower alkanoyl group, a hydroxy group, a cyano group, a phenyl group, a mono- or di-lower alkylaminocarbonyl group, or a group of the formula:

$$-P(=O)(OR_A)(OR_A)$$

wherein $R_1$ is a hydrogen atom or a lower alkyl group, and p is an integer of 1 to 4; and (d) a group of the formula:—Y—(CH$_2$)$_q$—Rd wherein Y is NH or S, Rd is a carboxyl group or a lower alkoxycarbonyl group, and q is an integer of 1 to 4;

$R_2$ is a hydrogen atom, a halogen atom, a lower alkyl group being optionally substituted by a hydroxy group, a hydroxy group, a lower alkoxy group, or a group of the above (b) or (c), or combines with $R_1$ to form a methylenedioxy group, said methylenedioxy group being optionally substituted by a carboxyl group or a lower alkoxycarbonyl group; $R_3$ is a hydrogen atom or a lower alkyl group; $R_4$ is a halogen atom or a trifluoromethyl group; and $R_5$ is a lower alkyl group, or a salt thereof.

3. The indole derivative according to claim 2, wherein $R_1$ bonds to the 5-, 6- or 7-position of the indole nucleus, and $R_2$ is a hydrogen atom, or a salt thereof.

4. The indole derivative according to claim 2, wherein $R_2$ is groups other than a hydrogen atom, one of $R_1$ and $R_2$ bonds to the 6-position of the indole nucleus, and the other bonds to the 7-position thereof, or a salt thereof.

5. The indole derivative according to claim 2, wherein $R_1$ is a lower alkyl group substituted by a hydroxy group, a phenylsulfonylamino group, a lower alkylsulfonylamino group, a di-lower alkylaminosulfonyl group, or a group selected from the following (a)[,(b-1),(c-1) or] to (d);

(a) a group of the formula:—X—Ra wherein X is O, S or NH, Ra is a hydrogen atom or a lower alkyl group, provided that when X is S, then Ra is a lower alkyl group;

(b) is (b-1) a group of the formula $$-\{O(CH_2)_m-CH\}_n-Rbb$$
$$\qquad\qquad\;|$$
$$\qquad\qquad Rb$$

wherein Rb[-1] is a hydrogen atom or a lower alkyl group, Rbb is a lower alkoxycarbonyl group or a carboxyl group, m is an integer of 0 to 3, and n is 0 or 1;

(c) is (c-1) a group of the formula:—O(CH$_2$)$_{p}$—Rc[-1] wherein Rc[-1] is a lower alkanoyl group, a phenyl group, a mono-lower alkylaminocarbonyl group, and p is an integer of 1 to 4; and (d) a group of the formula:—Y—(CH2)$_q$—Rd wherein Y is NH or S, Rd is a carboxyl group or a lower alkoxycarbonyl group, and q is an integer of 1 to 4;

R2 is a hydrogen atom, a halogen atom, a lower alkyl group being optionally substituted by a hydroxy group, a hydroxy group, a lower alkoxy group, or a group of the above (b-1) or (c-1), R3 is a hydrogen atom or a lower alkyl group; $R_4$ is a halogen atom or a trifluoromethyl group; and R5 is a lower alkyl group, or a salt thereof.

6. The indole derivative according to claim 2, wherein $R_1$ is a lower alkoxy group, a lower alkyl group, a lower alkoxycarbonyl group, a lower alkoxycarbonyl-lower alkoxy group, a carboxy-lower alkoxy group, a phenyl-lower alkoxy group, or a di-lower alkylaminosulfonyl group, $R_2$ is a hydrogen atom, a halogen atom, a lower alkoxy group, a lower alkyl group, a lower alkoxycarbonyl group, a lower alkoxycarbonyl-lower alkoxy group, a carboxy-lower alkoxy group or a phenyl-lower alkoxy group, $R_3$ is a hydrogen atom, $R_4$ is a halogen atom, and $R_5$ is a methyl group, or a salt thereof.

7. The indole derivative according to claim 6, wherein $R_1$ is a methoxy group, an ethoxy group, a methyl group, a methoxycarbonyl group, a methoxycarbonylmethoxy group, a carboxymethoxy group, a benzyloxy group, or a dimethylaminosulfonyl group, $R_2$ is a hydrogen atom or a methoxy group, $R_3$ is a hydrogen atom, $R_4$ is a chlorine atom, and $R_5$ is a methyl group, or a salt thereof.

8. The indole derivative according to claim 7, wherein $R_1$ is a methoxy group, an ethoxy group, a methoxycarbonyl group, a methoxycarbonylmethoxy group or a carboxymethoxy group, which bonds to the 6- or 7-position of the indole nucleus, $R_2$ and $R_3$ are a hydrogen atom, $R_4$ is a chlorine atom, and $R_5$ is a methyl group, or a salt thereof.

9. 2-[3-(7-Methoxyindol-3-yl)-2-propylamino]-1-(3-chlorophenyl)ethanol, or a salt thereof.

10. An optical isomer of 2-[3-(7-methoxyindol-3-yl)-2-propylamino]-1-(3-chlorophenyl)ethanol, or a salt thereof.

11. 2-[3-(7-Ethoxyindol-3-yl)-2-propylamino]-1-(3-chlorophenyl)ethanol, or a salt thereof.

12. An optical isomer of 2-[3-(7-ethoxyindol-3-yl)-2-propylamino]-1-(3-chlorophenyl)ethanol, or a salt thereof.

13. 2-[3-(7-Methoxycarbonylmethoxyindol-3-yl)-2-propylamino]-1-(3-chlorophenyl)ethanol, or a salt thereof.

14. An optical isomer of 2-[3-(7-methoxycarbonylmethoxyindol-3-yl)-2-propylamino]-1-(3-chlorophenyl)ethanol, or a salt thereof.

15. 2-[3-(7-Carboxymethoxyindol-3-yl)-2-propylamino]-1-(3-chlorophenyl)ethanol, or a salt thereof.

16. An optical isomer of 2-[3-(7-Carboxymethoxyindol-3-yl)-2-propylamino]-1-(3-chlorophenyl)ethanol, or a salt thereof.

17. A β3-adrenergic receptor-stimulating composition, which comprises as an active ingredients a therapeutically effective amount of the indole derivative as set forth in claim 1, or a pharmaceutically acceptable salt thereof, and a pharmaceutically acceptable carrier or diluent.

18. A composition for treatment of diabetes mellitus, which comprises as an active ingredient, a therapeutically effective amount of the indole derivative as set forth in claim 1, or a pharmaceutically acceptable salt thereof, and a pharmaceutically acceptable carrier or diluent.

19. A composition for treatment of obesity, which comprises as an active ingredient, a therapeutically effective amount of the indole derivative as set forth in claim 1, or a pharmaceutically acceptable salt thereof, and a pharmaceutically acceptable carrier or diluent.

20. A pharmaceutical composition which comprises the indole derivative set forth in claim 1 or a pharmaceutically acceptable salt and a pharmaceutically acceptable carrier or diluent.

21. A method for treatment of diabetes mellitus in mammals, which comprises administering to said mammal a therapeutically effective amount of the indole derivative as set forth in claim 1, or a pharmaceutically acceptable salt thereof.

22. A method for treatment of obesity in mammals, which comprises administering to said mammal a therapeutically effective amount of the indole derivative as set forth in claim 1, or a pharmaceutically acceptable salt thereof.

23. A process for preparing the indole derivative of the formula I as set forth in claim 1 or a salt thereof, which comprises reacting a compound of the formula III:

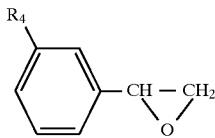

wherein $R_4$ is a halogen atom or a trifluoromethyl group, with a compound of the formula IV:

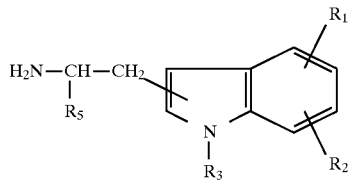

wherein $R_1$ is a lower alkyl group being optionally substituted by a hydroxy group, a phenylsulfonylamino group, a lower alkylsulfonylamino group, a mono- or di-lower alkylamino-sulfonyl group, or a group selected from the following (a) to (d), or combines with $R_2$ to form a methylenedioxy group, said methylenedioxy group being optionally substituted by a carboxyl group or a lower alkoxycarbonyl group, (a) a group of the formula:—X—Ra, wherein X is O, S or NH, Ra is a hydrogen atom or a lower alkyl group, provided that when X is S, then Ra is a lower alkyl group;

(b) a group of the formula:

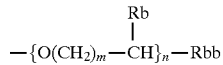

wherein Rb is a hydrogen atom, a lower alkyl group, a lower alkoxycarbonyl group or a carboxyl group, Rbb is a lower alkoxycarbonyl group or a carboxyl group, m is an integer of 0 to 3, and n is 0 or 1;

(c) a group of the formula:—O(CH$_2$)$_p$—Rc, wherein Rc is a lower alkanoyl group, a hydroxy group, a cyano group, a phenyl group, a mono- or di-lower alkylaminocarbonyl, or a group of the formula:

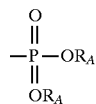

wherein $R_1$ is a hydrogen atom or a lower alkyl group, and p is an integer of 1 to 4;

(d) a group of the formula:—Y—(CH$_2$)$_q$—Rd, wherein Y is NH or S, Rd is a carboxyl group or a lower alkoxycarbonyl group, and q is an integer of 1 to 4; and $R_2$ is a hydrogen atom, a halogen atom, a lower alkyl group, being optionally substituted by a hydroxy group, a hydroxy group, a lower alkyl group, or a group of the above (b) or (c), or combines with $R_1$ to form a methylenedioxy group being optionally substituted by a carboxyl group; $R_3$ is a hydrogen atom or a lower alkyl group; and $R_5$ is a lower alkyl group, or a salt thereof.

24. A process for preparing a compound of formula I-b:

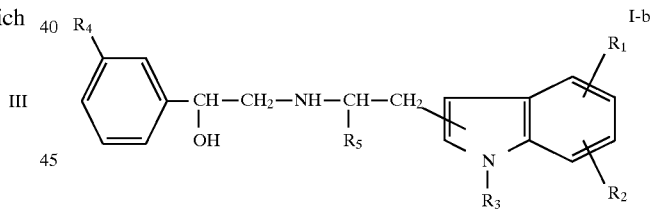

wherein $R_1$' is a lower alkyl group being optionally substituted by a hydroxy group, a phenylsulfonylamino group, a lower alkylsulfonylamino group, a mono- or di-lower alkylaminosulfonyl group, or a group selected from the following (a)', (b), (c) and (d)', or combines with $R_2$ to form a methylenedioxy group, said methylenedioxy group being optionally substituted by a carboxyl group or a lower alkoxycarbonyl group, (a)' a group of the formula —X'—Ra wherein X' is O or S, Ra is a hydrogen atom or a lower alkyl group, provided that when X' is S, then Ra is a lower alkyl group;

(b) a group of the formula

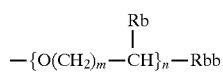

wherein Rb is a hydrogen atom, a lower alkyl group, a lower alkoxycarbonyl group or a carboxyl group, Rbb is a lower alkoxycarbonyl group or a carboxyl group, m is an integer of 0 to 3, and n is 0 or 1;

(c) a group of the formula:—O(CH$_2$)$_p$—Rc wherein Rc is a lower alkanoyl group, a hydroxy group, a cyano group, a phenyl group, a mono- or di-lower alkylaminocarbonyl group, or a group of the formula:

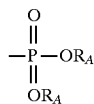

wherein R$_A$ is a hydrogen atom or a lower alkyl group, and p is an integer of 1 to 4;

(d)' a group of the formula:—Y'—(CH$_2$)$_q$—Rd wherein Y' is S, Rd is a carboxyl group or a lower alkoxycarbonyl group, and a is an integer of 1 to 4;

R$_2$ is a hydrogen atom, a halogen atom, a lower alkyl group being optionally substituted by a hydroxy group, a hydroxy group, a lower alkoxy group, or a group of the above (b) or (c), or combines with R$_1$ to form a methylenedioxy group, said methylenedioxy group being optionally substituted by a carboxyl group or a lower alkoxycarbonyl group; R$_3$ is a hydrogen atom or a lower alkyl group; R$_4$ is a halogen atom or a trifluoromethyl group, and R$_5$ is a lower alkyl group, or a salt thereof, which comprises reacting a compound of the formula V:

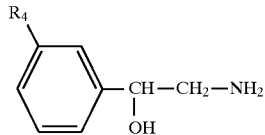

wherein R$_4$ is a halogen atom or a trifluoromethyl group, with a compound of the formula VI:

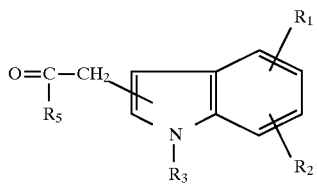

wherein R$_1$', is the same as defined above, and R$_2$, R$_3$, and R$_5$ are the same as defined above, under reducing conditions.

25. A process for preparing a compound of formula I-c:

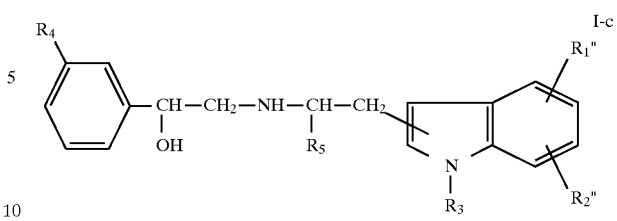

wherein R$_1$" is a lower alkyl group being optionally substituted by a hydroxy group, a phenylsulfonylamino group, a lower alkylsulfonylamino group, a mono- or di-lower alkylaminosulfonyl group, or a group selected from the following (a) or (c)", or combines with R$_2$" to form a methylenedioxy group, (a) a group of the formula:—X—Ra wherein X is O, S or NH, Ra is a hydrogen atom or a lower alkyl group, provided that when X is S, then Ra is a lower alkyl group;

(c)" a group of the formula:—O(CH$_2$)$_p$—Rc" wherein Rc" is a hydroxy group, a phenyl group, or a group of the formula:

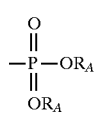

wherein R$_A$ is a hydrogen atom or a lower alkyl group, and p is an integer of 1 to 4, R$_2$" is a hydrogen atom, a halogen atom, a lower alkyl group being optionally substituted by a hydroxy group, a hydroxy group, a lower alkoxy group, or the group of the above (c)", or combines R$_1$" to form a methylenedioxy group, R$_3$ is a hydrogen atom or a lower alkyl group; R$_4$ is a halogen atom or a trifluoromethyl group; and R$_5$ is a lower alkyl group, or a salt thereof, which comprises subjecting a compound of the formula VII:

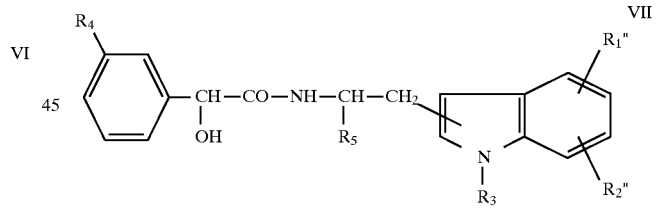

wherein R$_1$", R$_2$" are the same as defined above and R$_3$, R$_4$ and R$_5$ are the same as defined above, to reduction.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 43 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc = "chemically synthetic DNA"

( x i ) SEQUENCE DESCRIPTION: SEQ ID NO:1:

AGCTCCTGCA GGCGCGCCGA TATCTCGAGC GGCCGCGGTA CCA    43

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "chemically synthetic DNA"

( x i ) SEQUENCE DESCRIPTION: SEQ ID NO:2:

CCACCTGCAG GTGATTTGGG AGACCCC    27

( 2 ) INFORMATION FOR SEQ ID NO:3:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: other nucleic acid ( A ) DESCRIPTION: /desc = "chemically synthetic DNA"

( x i ) SEQUENCE DESCRIPTION: SEQ ID NO:3:

TTCTCGAGCC GGGGAATCCC ATGGGAC 27

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthetic DNA"

( x i ) SEQUENCE DESCRIPTION: SEQ ID NO:4:

ACACCTGCAG GTGAGGCTTC CAGGCGTCC 29

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthetic DNA"

( x i ) SEQUENCE DESCRIPTION: SEQ ID NO:5:

TGTAAGCTTC TGCTTTACAG CAGTGAGTC 29